(12) United States Patent
Phillips et al.

(10) Patent No.: US 11,314,943 B2
(45) Date of Patent: *Apr. 26, 2022

(54) TYPIFYING EMOTIONAL INDICATORS FOR DIGITAL MESSAGING

(71) Applicant: Capital One Services, LLC, McLean, VA (US)

(72) Inventors: Jeremy Phillips, Brooklyn, NY (US); Andrew Beane, New York, NY (US)

(73) Assignee: Capital One Services, LLC, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/992,241

(22) Filed: Aug. 13, 2020

(65) Prior Publication Data

US 2020/0372221 A1   Nov. 26, 2020

Related U.S. Application Data

(63) Continuation of application No. 16/410,042, filed on May 13, 2019, now Pat. No. 10,776,584, which is a
(Continued)

(51) Int. Cl.
| | |
|---|---|
| *G06F 40/30* | (2020.01) |
| *G06K 9/00* | (2006.01) |
| *G06F 3/0484* | (2013.01) |
| *G06F 3/0481* | (2013.01) |
| *G08B 21/18* | (2006.01) |
| *A61B 5/00* | (2006.01) |
| *A61B 5/01* | (2006.01) |
| *A61B 5/021* | (2006.01) |
| *A61B 5/16* | (2006.01) |

(Continued)

(52) U.S. Cl.
CPC ............ *G06F 40/30* (2020.01); *A61B 5/0077* (2013.01); *A61B 5/01* (2013.01); *A61B 5/021* (2013.01); *A61B 5/165* (2013.01); *A61B 5/6898* (2013.01); *A61B 5/7264* (2013.01); *G06F 3/0484* (2013.01); *G06F 3/04817* (2013.01); *G06F 40/253* (2020.01); *G06K 9/00302* (2013.01); *G08B 21/18* (2013.01)

(58) Field of Classification Search
None
See application file for complete search history.

(56) References Cited

U.S. PATENT DOCUMENTS

| | | | | |
|---|---|---|---|---|
| 9,479,470 B2 * | 10/2016 | Song | ................. | H04L 51/36 |
| 9,525,753 B2 * | 12/2016 | Shah | ................. | H04L 51/32 |

(Continued)

FOREIGN PATENT DOCUMENTS

| | | | | |
|---|---|---|---|---|
| WO | WO-2018104834 A1 * | 6/2018 | ............. | G06F 3/011 |
| WO | WO-2020021319 A1 * | 1/2020 | ............. | G06T 13/40 |

*Primary Examiner* — Fekadeselassie Girma
(74) *Attorney, Agent, or Firm* — Kacvinsky Daisak Bluni PLLC

(57) ABSTRACT

The present disclosure provides computing systems and techniques for indicating an emotional and/or environmental state of a user in a digital messaging application. A computing device can determine an emotional and/or environmental state of a first user responsive to reading or responding to a message and can convey the determined emotional and/or environmental state to a second computing device, to be transiently presented by the second computing device.

20 Claims, 11 Drawing Sheets

Related U.S. Application Data continuation of application No. 16/153,096, filed on Oct. 5, 2018, now Pat. No. 10,346,541.

(51) Int. Cl.
  *G06F 40/253* (2020.01)
  *G06F 3/04817* (2022.01)

(56) References Cited

U.S. PATENT DOCUMENTS

| | | | | |
|---|---|---|---|---|
| 9,998,883 | B2* | 6/2018 | Arimilli | G06F 3/0481 |
| 10,021,152 | B2* | 7/2018 | Lohe | H04L 12/1822 |
| 10,063,620 | B2* | 8/2018 | Lin | H04L 67/06 |
| 10,069,880 | B2* | 9/2018 | Fan | G06F 16/9566 |
| 10,147,102 | B2* | 12/2018 | Zamer | G06Q 20/102 |
| 2008/0222295 | A1* | 9/2008 | Robinson | G06Q 10/10 |
| | | | | 709/227 |
| 2013/0018960 | A1* | 1/2013 | Knysz | H04L 65/403 |
| | | | | 709/204 |
| 2013/0086167 | A1* | 4/2013 | Blom | G06Q 50/01 |
| | | | | 709/204 |
| 2013/0103759 | A1* | 4/2013 | Blom | H04W 4/21 |
| | | | | 709/204 |
| 2013/0325462 | A1* | 12/2013 | Somekh | G06F 16/58 |
| | | | | 704/235 |
| 2013/0340086 | A1* | 12/2013 | Blom | G06F 21/6245 |
| | | | | 726/26 |
| 2014/0007010 | A1* | 1/2014 | Blom | G06F 3/0481 |
| | | | | 715/825 |
| 2014/0070947 | A1* | 3/2014 | Ionson | G08B 31/00 |
| | | | | 340/541 |
| 2014/0129627 | A1* | 5/2014 | Baldwin | G06Q 10/10 |
| | | | | 709/204 |
| 2014/0289323 | A1* | 9/2014 | Kutaragi | H04L 67/42 |
| | | | | 709/203 |
| 2015/0262507 | A1* | 9/2015 | Hanlon | G09B 19/0092 |
| | | | | 434/127 |
| 2015/0304369 | A1* | 10/2015 | Sandholm | H04L 51/32 |
| | | | | 715/753 |
| 2016/0352887 | A1* | 12/2016 | Na | H04M 1/72409 |
| 2016/0359777 | A1* | 12/2016 | Tucker | H04L 51/16 |
| 2017/0078621 | A1* | 3/2017 | Sahay | H04N 7/185 |
| 2018/0211660 | A1* | 7/2018 | Bastide | A61M 21/02 |

* cited by examiner

*State Indication*
*800*

*State Indication*
*900*

*State Indication*
*1000*

TYPIFYING EMOTIONAL INDICATORS FOR DIGITAL MESSAGING

CROSS-REFERENCE TO RELATED APPLICATION

This application is a Continuation of U.S. patent application Ser. No. 16/410,042, filed May 13, 2019, which is a Continuation of U.S. patent application Ser. No. 16/153,096, filed Oct. 5, 2018 (issued as U.S. Pat. No. 10,346,541 on Jul. 9, 2019). The contents of both aforementioned patent applications are incorporated herein by reference in their entireties.

TECHNICAL FIELD

Examples described herein are generally related to digital messaging and particularly to conveying an emotional state along with a message or while a message is being composed.

BACKGROUND

Modern communication devices typically include digital messaging capabilities. For example, computers, tablets, mobile phones, etc. all include the ability to execute digital messaging applications, where users can send and receive messages from other users of such devices. Some digital messaging applications provide indicators (e.g., three dots) that another user is typing a message. However, such digital messaging applications do not currently provide an ability to indicate an emotional and/or environmental state. The present disclosure is directed towards providing an indication of an emotional and/or environmental state.

DETAILED DESCRIPTION

Figure 1B:
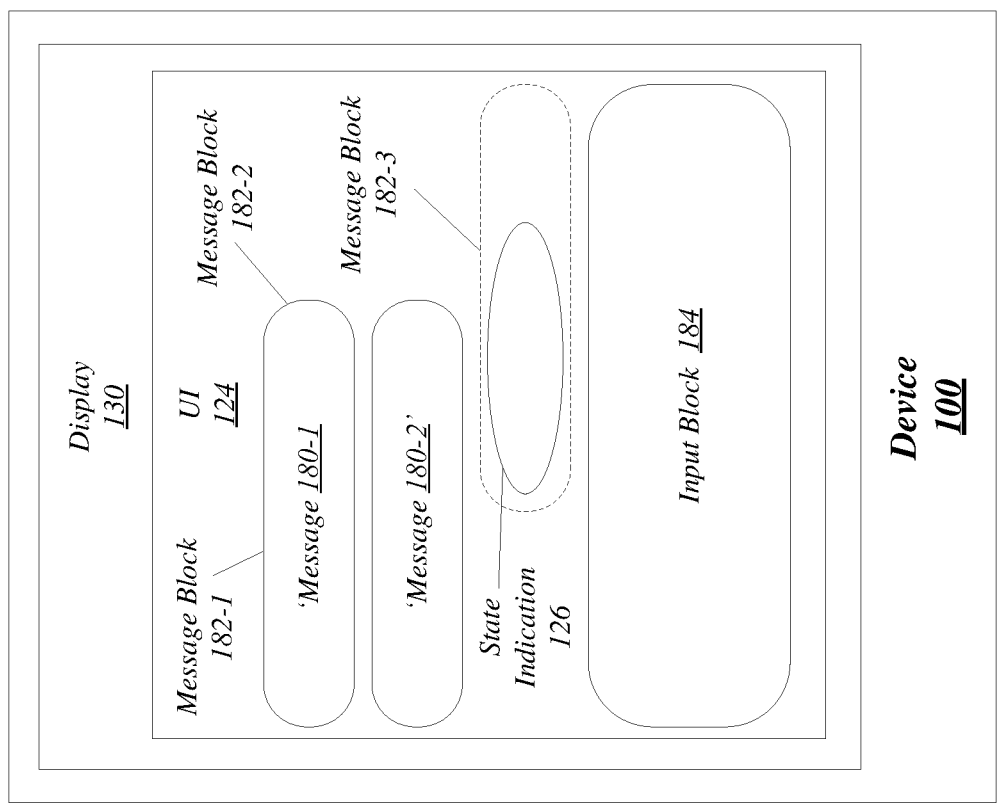
FIG. 1B illustrates a first example user interface, displayed on the computing device of FIG. 1A.

As contemplated in the present disclosure, an indication of an emotional and/or environmental state of a user can be provided to another user. Such an indication can be presented, for example, transiently, to convey the emotional and/or environmental state of the user. It is noted, the present disclosure enables providing indications of emotional and/or environmental states faster than the user could convey the information manually. Furthermore, the present disclosure enables providing the indications of emotional and/or environmental states in a manner than may be seamless to the end user.

More particularly, the disclosure can be implemented to provide indications of emotional and/or environmental state during a messaging transaction. For example, the indication can be provided to a message sender in response to a message receiver receiving a message from the sender and for a transient period associated with when the message receiver is responding to and/or reviewing the received message. Once a response message is sent to the sender by the receiver, the indication can be withdrawn, removed, or for example, replaced with the response message.

In some examples, a first user interacting with a first computing device can receive a message from a second user interacting with a second computing device, via the first computing devices. The first computing device can determine an emotional and/or environmental state of the first user responsive to reading and/or responding to the message and can convey the determined emotional and/or environmental state to the second computing device, to be transiently presented by the second computing device.

With some implementations, an emotional state can be determined based on biometric data, for example, captured by a wearable device coupled to the computing device with which the first user is interacting. In some implementations, an emotional state can be determined based on one or more characteristics of how the first user is interacting with the computing device (e.g., typing speed, typing pressure, etc.).

In some implementations, an environmental state can be determined based on various factors, such as, an application (e.g., map application, internet browsing application, office application, telephone application, or the like) being actively used by the first user. With some implementations, an environmental state can be determined based on whether the computing device is in movement, whether the computing device is coupled to a vehicle, or the like. Furthermore, environmental state can be determined based on location data for the computing device (e.g., at home, in bed, at an office, in a conference room of an office, or the like.

The computing device can generate an indicator of the emotional state, the environmental state, or a combination of the emotional and environmental state. With some implementations, the indicator can be an emoji, a combination of emojis, a punctuation mark, a combination of punctuation marks, or coloring of an emoji and/or punctuation mark. This indicator can be conveyed to the second computing device for presentation in a user interface to indicate, to the second user, the emotional and/or environmental state of the first user.

Figure 1A:
FIG. 1A illustrates an example computing device.

FIGS. 1A and 1B illustrate an example computing device 100 and a user interface (UI) 124 for a digital messaging application 122. More specifically, FIG. 1 depicts the device 100 and associated components of the device 100 while FIG. 1B depicts the UI 124 displayed on a display 130 of the device.

The computing device 100 can include, at least in part, a processor 110, a memory 120, a display 130, an interface 140, input/output (I/O) component(s) 150, sensor(s) 160, and a radio 170. The memory 120 may store the digital messaging application 122, the UI 124, state indication 126, and state data 128. In general, responsive to executing the digital messaging application 122 on the computing device 100; the computing device 100 can send and receive messages with another computing device (see FIG. 2) and can generate the UI 124 including indications of the sent and received messages. Computing device 100, in executing digital messaging application 122 can capture state data 128, responsive to a user receiving message(s), reading the messages, or replying to the messages; and can determine an emotional and/or environmental state of the user of the computing device 100 based on the state data 128. Computing device 100, in executing digital messaging application 122 can generate an indication (state indication 126) of the determined emotional and/or environmental state, as further discussed herein. Furthermore, computing device 100, in executing digital messaging application 122, can send the state indication 126 to the other computing device and can present the state indication 126 in the UI 124.

With some examples, the processor 110 may include circuitry or processor logic, such as, for example, any of a variety of commercial processors. In some examples, the processor 110 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 110 may include graphics processing portions and may include dedicated memory, multiple-threaded processing and/or some other parallel processing capability.

The memory 120 may include logic, a portion of which includes arrays of integrated circuits, forming non-volatile memory to persistently store data or a combination of non-volatile memory and volatile memory. It is to be appreciated, that the memory 120 may be based on any of a variety of technologies. In particular, the arrays of integrated circuits included in memory 120 may be arranged to form one or more types of memory, such as, for example, dynamic random access memory (DRAM), NAND memory, NOR memory, or the like.

Display 130 can be based on any of a variety of display technologies, such as, for example, a cathode ray tube (CRT), a liquid crystal display (LCD), plasma display, light emitting diode (LED) display, or an organic light emitting diode (OLED) display. With some examples, display 130 can be a touch sensitive display. It is noted, display 130 may be external to the computing device 100, such as, for example, embodied as a computer monitor or television and coupled to the computing device 100 via any of a variety of display data interfaces.

Interface 140 may include logic and/or features to support a communication interface. For example, the interface 140 may include one or more interfaces that operate according to various communication protocols or standards to communicate over direct or network communication links. Direct communications may occur via use of communication protocols or standards described in one or more industry standards (including progenies and variants). For example, the interface 140 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like.

The I/O component(s) 150 may include one or more components to provide input to or to provide output from the computing device 100. For example, the I/O component(s) 150 may be a keyboard (hardware, virtual, etc.), mouse, joystick, microphone, track pad, button, touch layers of a display, haptic feedback device, camera, microphone, speaker, or the like.

The sensor(s) 160 may include a number of any of a variety of sensors arranged to detect information, such, as, physical surrounding information, geo-information, biometric information, or the like. For example, sensor(s) 160 can include a radar sensor, infrared sensors, light sensors, RFID sensors, gyroscopes, a global positioning sensors (GPS), a heart rate sensor, a temperature sensor, or the like. Signals from sensor(s) 160 can be used to an emotional and/or environmental state of a user of the computing device 100, as discussed in greater detail below. It is noted, that some of the sensor(s) 160 could be located externally to the computing device 100, such as, for example, on a wearable device (e.g., see FIG. 11).

The radio 170 may include circuitry arranged to communicate data with one or more other devices (see FIG. 2) via any of a variety of communication protocols. Such communication may involve communication across one or more networks, such a wireless local area networks (WLAN) or cellular network. In some examples, radio 170 can be arranged to communicate via Wi-Fi, Bluetooth, Zigbee, LTE, 5G, or the like.

During operation of computing device 100, processor 110 can execute the digital messaging application to 122 to send, receive, or both send and receive messages 180 from another computing device. Often, the messages 180 are relayed between the computing device via the radio 170 and a network (e.g., cellular network, the Internet, etc.). For example, the computing device 100 can send and receive information elements to another computing device including indications of the messages 180.

The processor 110, in executing the digital messaging application 122, can generate the UI 124 to present the messages to a user. For example, UI 124 can include message blocks 182 to present the messages to a user. UI 124 is depicted including message blocks 182-1, 182-2, and 182-3. Specifically, message blocks 182-1 and 182-2 are depicted displaying messages 180-1 and 180-2. The UI 124 can further include an input block 184 arranged to receive input from a user. For example, the user can provide content for a message 180 via the input block 184.

It is to be appreciated that a variety of techniques for indicating a sender or receiver of a message 180 exist. For example, as depicted in UI 124, messages 180 received by a user of computing device 100 on which UI 124 is displayed are aligned on the left side of the screen while messages sent by the user, via computing device 100, are aligned on the right side of the screen. Accordingly, messages 180-1 and 180-2 displayed in message blocks 182-1 and 182-2 were received by the user of the computing device 100. Message block 182-3 corresponds to a message to be sent, via computing device 100, by the user.

Message block 182-3 is used to depict, often transiently, the state indication 126. The state indication 126 can determined by computing device 100 (as discussed further herein) and can be provided to indicate an emotional state of the user (e.g., the user of computing device 100), an environmental state of the user, or both an emotional and environmental state of the user. In general, the state indication 126 can comprise any number of indicators (e.g., emojis, colored emojis, punctuation marks, colored punctuation marks, or the like). A number of examples of a state indication 126 are given in FIGS. 7-12.

Figure 2:
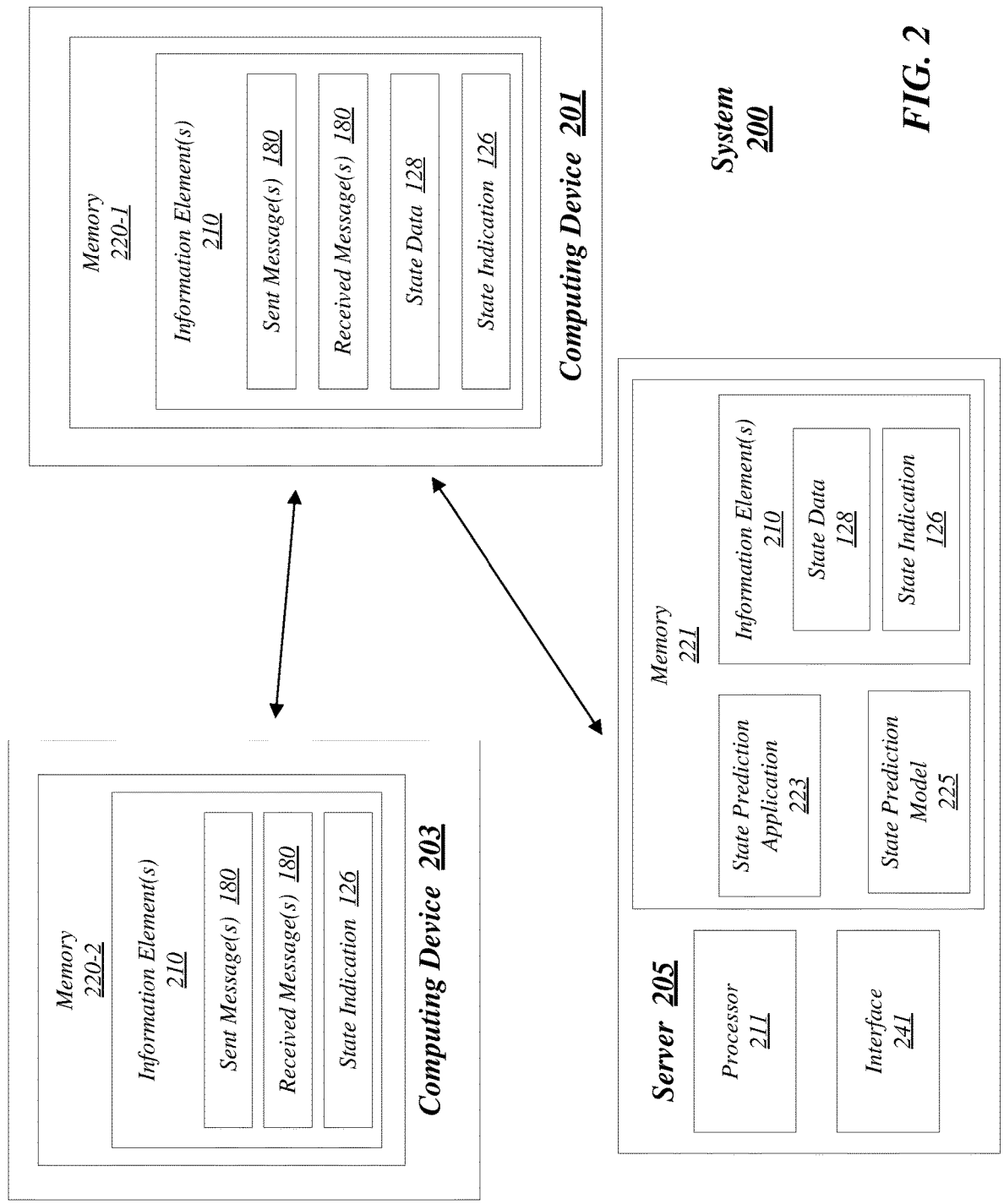
FIG. 2 illustrates a first example system.

FIG. 2 illustrates an example system 200 including computing device 201, another computing device 203, and a server 205. In general, the computing devices 201 and 203 can be like the computing device 100 of FIGS. 1A and 1B. However, for purposes of clarity of presentation, the computing device 201 and 203 are only depicted including a memory. Specifically, computing device 201 is depicted including memory 220-1 and computing device 203 is depicted including memory 220-2. However, the computing devices 201 and 203 will also typically include other components depicted in FIG. 1A, for example, processor 110, display 130, radio 170, etc.

The server 205 can include, at least in part, a processor 211, a memory 221, and an interface 241. The memory 221 may store a state prediction application 223, a state prediction model 225, information element(s) 210, state data 128 and state indication 126.

With some examples, the processor 211 may include circuitry or processor logic, such as, for example, any of a variety of commercial processors. In some examples, the processor 211 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 211 may include graphics processing portions and may include dedicated memory, multiple-threaded processing and/or some other parallel processing capability.

The memory 221 may include logic, a portion of which includes arrays of integrated circuits, forming non-volatile memory to persistently store data or a combination of non-volatile memory and volatile memory. It is to be appreciated, that the memory 221 may be based on any of a variety of technologies. In particular, the arrays of integrated circuits included in memory 221 may be arranged to form one or more types of memory, such as, for example, dynamic random access memory (DRAM), NAND memory, NOR memory, or the like.

Interface 241 may include logic and/or features to support a communication interface. For example, the interface 241 may include one or more interfaces that operate according to various communication protocols or standards to communicate over direct or network communication links. Direct communications may occur via use of communication protocols or standards described in one or more industry standards (including progenies and variants). For example, the interface 241 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like.

Figure 3:
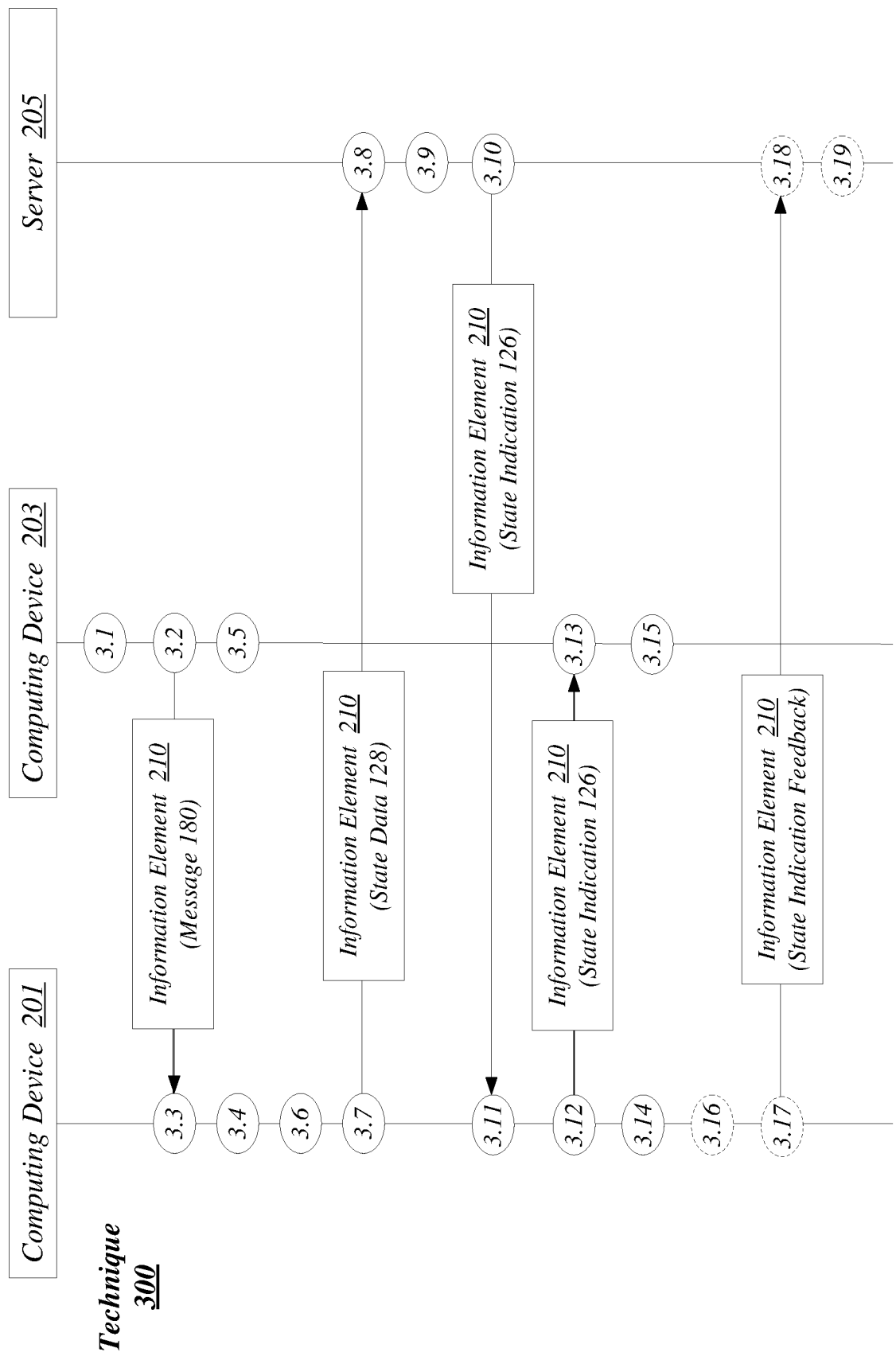
FIG. 3 illustrates an example technique to provide an indication of emotional and/or environmental state in a digital messaging application.

Computing device 201 can be communicatively coupled with both the computing device 203 and the server 205. For example, computing device 201 can be communicatively coupled to computing device 203 and server 205 via a network (e.g., cellular, Wi-Fi, the Internet, or the like). An example operation of the system 200 is described with reference to the technique 300 of FIG. 3. In general, FIG. 3 depicts a technique to provide an indication of an emotional and/or environmental state in a digital messaging application (e.g., digital messaging application 122, or the like). It is noted, technique 300 is described with reference to the system 200 of FIG. 2 and the computing device 100 and UI 124 of FIGS. 1A and 1B. This is done for purposes of convenience and clarity, as opposed to limitation. For example, technique 300 could be implemented by a system having a different arrangement or entities from that of the system 200 of FIG. 2. Additionally, it is noted that although server 205 and operations of server 205 are discussed separately and distinct from that of operations of computing device 201 and/or 203; in some implementations features described with respect to server 205 can be embodied by either or both of computing device 201 and 203. For example, computing device 201 and 203 can include state prediction application 223 and state prediction model 225. Examples are not limited in this context.

Turning now to FIG. 3, technique 300 can begin at circle 3.1. At circle 3.1, computing device 203 can generate an information element 201 including an indication of a message (or messages) for computing device 201. For example, a processor (e.g., processor 110, or the like) of computing device 203, in executing a digital messaging application (e.g., digital messaging application 122, or the like) can generate information element 210 including an indication of messages 180 for a user associated with computing device 201. With some implementations, computing device 203 can generate the information element responsive to receiving input from a user indicating the contents of messages 180.

Continuing to circle 3.2, computing device 203 can send the information element 210 to computing device 201. For example, a processor of computing device 203, in executing the digital messaging application, can send the information element 210 including indications of the message 180 to computing device 201 (e.g., via radio 170, or the like). At circle 3.3, computing device 201 can receive the information element 210 including the indication of message 180. For example, a processor (e.g., processor 110, or the like) of computing device 201, in executing a digital messaging application (e.g., digital messaging application 122, or the like) can receive (e.g., via radio 170, or the like) the information element 210 including an indication of the messages 180 from a user associated with computing device 203.

Continuing to circle 3.4 and circle 3.5, computing devices 201 and 203, respectively, can present the message 180 in a UI displayed on a display associated with the respective computing device. For example, a processor of computing device 201, in executing the digital messaging application can present the message 180 (e.g., in a message block 182, or the like) in a UI (e.g., UI 124, or the like) displayed on a display (e.g., display 130, or the like) of computing device 201. Likewise, a processor of computing device 203, in executing the digital messaging application can present the message 180 (e.g., in a message block 182, or the like) in a UI (e.g., UI 124, or the like) displayed on a display (e.g., display 130, or the like) of computing device 203.

Continuing to circle 3.6. At circle 3.6, computing device 201 can capture, determine, or otherwise generate state data 128. In general, state data 128 can comprise indications of characteristics of computing device 201 and/or characteristics of a user of computing device 201, responsive to receiving message 180, reading message 180, ore replying to message 180. Said differently, at circle 3.6, computing device 201 can capture characteristics of computing device 201 and/or of a user of computing device 201 at the time the user interacts with the message 180 (e.g., via a UI, or the like). This is described in greater detail below, for example, with respect to FIG. 4-6. However, in general, state data 128 can comprise characteristics of computing device 201, such as, for example, a currently actively used application, current state of movement (e.g. in motion, not in motion, velocity, etc.), state of connection of accessories (e.g., a vehicle, or the like), location data, etc. Furthermore, state data 128 can comprise biometric data of a user of the device, an image captured of the user, or characteristics of how the user is interacting with the computing device (e.g., typing speed, typing pressure, etc.). Also, at circle 3.6, computing device 201 can generate an information element 210 including indications of the state data 128.

Continuing to circle 3.7, computing device 201 can send the information element 210 to server 205. For example, a processor of computing device 201, in executing the digital messaging application, can send the information element 210 including indications of the state data 128 to server 205. At circle 3.8, server 205 can receive the information element 210 including the indication of state data 128. For example, processor 211 of server 205, in executing state prediction application 223, can receive (e.g., via interface 241, or the like) the information element 210 including an indication of the state data 128 from computing device 201.

Continuing to circle 3.9. At circle 3.9, server 205 can generate a state indication 126 based in part on the state data 128. For example, server 205 can generate state indication 126 from state data 128 and state prediction model 225. Said differently, processor 211, in executing state prediction application 223 can generate state indication 126 via at least providing state data 128 as inputs to state prediction model 225. In some examples, state prediction model 225 can be a machine learning model (e.g., a neural network, or the like). Server 205 (or processor 211 in executing state prediction application 223) can use state prediction model 225 to generate indications of an emotional and/or environmental state of a user of computing device 201 based on state data 128. Also, at circle 3.9, server 205 can generate an information element 210 including indications of the state indication 126.

Continuing to circle 3.10, server 205 can send the information element 210 to computing device 201. For example, a processor of server 205, in executing the state prediction application, can send the information element 210 including indications of the state indication 126 to computing device 201. At circle 3.11, computing device 201 can receive the information element 210 including the indication of state indication 126. For example, a processor of computing device 201, in executing a digital messaging application, can receive (e.g., via radio 170, or the like) the information element 210 including an indication of the state indication 126 from server 205.

Continuing to circle 3.12, computing device 201 can send an information element 210 including an indication of state indication 126 to computing device 203. With some examples, computing device 201 relays the information element 210 received from the server 205. In other example, computing device 201 generates a new information element 210 including an indication of state data 126 and send this information element 210 to computing device 203. In some examples, computing device 201 generates a custom state indication 126 based on user preferences associated with the digital messaging application executed on computing device 201. This is described in greater detail below, for example, with respect to FIGS. 7-12.

At circle 3.13, computing device 203 can receive the information element 210 including the indication of state indication 126. For example, a processor of computing device 203, in executing a digital messaging application, can receive (e.g., via radio 170, or the like) the information element 210 including an indication of the state indication 126 from computing device 201.

Continuing to circle 3.14 and circle 3.15, computing devices 201 and 203, respectively, can present the state indication 126 in a UI displayed on a display associated with the respective computing device. For example, a processor of computing device 201, in executing the digital messaging application can present the state indication 126 (e.g., in a message block 182, or the like) in a UI (e.g., UI 124, or the like) displayed on a display (e.g., display 130, or the like) of computing device 201. Likewise, a processor of computing device 203, in executing the digital messaging application can present the state indication 126 (e.g., in a message block 182, or the like) in a UI (e.g., UI 124, or the like) displayed on a display (e.g., display 130, or the like) of computing device 203. In some examples, computing devices 201 and 203 can transiently present the state indication 126. In some examples, only computing device 203 can present the state indication 126.

Technique 300 can optionally, include circles 3.16 to 3.19. At circle 3.16, computing device 201 can generate feedback respective to state indication 126. For example, a user of computing device 201 can select an alternative state indication to present and to send to computing device 201. The alternative state indication can be sent to server 205 in an information element 210 at circle 3.17 as state indication feedback. At circle 3.18, server 205 can receive the information element with state indication feedback and at circle 3.19, server 205 can update state prediction model 225 based on the state indication feedback. For example, processor 211 in executing state prediction application 223 can further train state prediction model 225 using state indication feedback.

Figure 4:
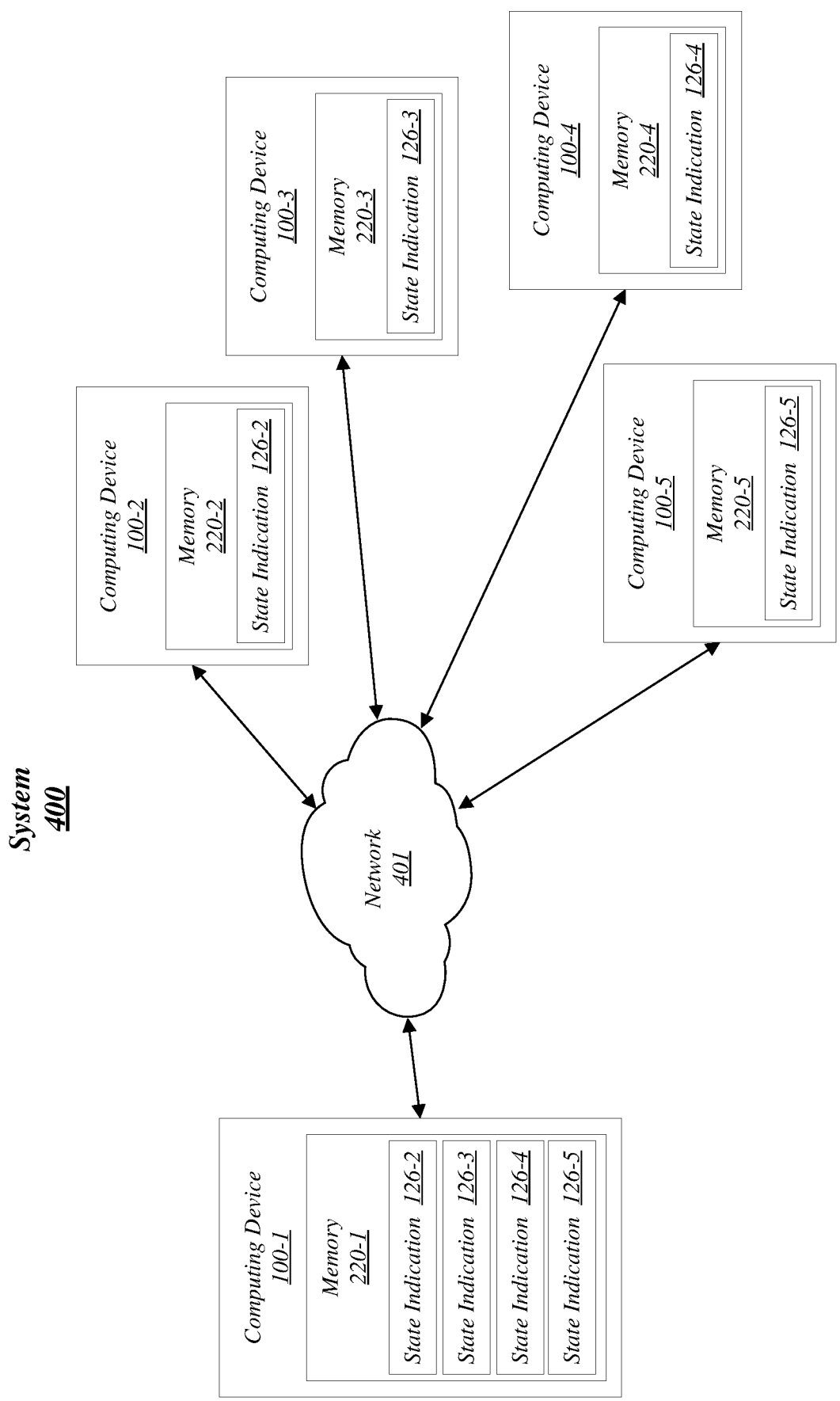
FIG. 4 illustrates a second example system.

It is noted, that the above example discusses providing indications of emotional and/or environmental states between two users (e.g., user of computing device 201 and 203). However, in practice, the present disclosure can be implemented to enable providing indications of emotional and/or environmental states of multiple users, for example, users engaged in a conference, group discussion, or the like. FIG. 4 illustrates an example system 400 including a number of computing devices 100, coupled via network 401. Network 401 could be, for example, a local area network (LAN), a wide area network (WAN), or a cellular network (e.g., LTE, 3GPP, or the like). In some embodiments, network 401 could include the Internet.

System 400 is depicted including computing devices 100-1, 100-2, 100-3, 100-4 and 100-5. It is noted that the number of computing devices is given for purposes of clarity of presentation and not to be limiting. Embodiments can be provided with more of less computing devices than depicted in this figure. During operation, ones of the computing devices 100 can provide state indications to another one of the computing devices 100. For example, during a group discussion, a single user may be presenting, talking, or otherwise communicating with a group, or audience. Computing devices associated with members of the group of audience can provide state indications 126 to a computing device associated with the user presenting, talking, or otherwise communicating. For example, computing devices 100-2 to 100-5 are depicted with memory 220-2 to 220-5 and state indications 126-2 to 126-5, respectively.

During operation, computing devices 100-2 to 100-5 can determine a state indication 126 as described herein. Furthermore, computing device 100-2 to 100-5 can provide the respective state indications 126 to computing device 100-1. Computing device 100-1 is depicted including memory 220-1 and state indications 126-2 to 126-5, corresponding to emotional and/or environmental state determined by respective computing device 100-2 to 100-5. Computing device 100-1 can be configured to present the state indications 126-2 to 126-5 as described herein to convey an indication of the emotional and/or environmental state of the "audience" to which the user of computing device 100 is communicating. In this manner, of the "presenter" can gauge the response of the audience to recent communications and could adapt or adjust the message accordingly.

Figure 5:
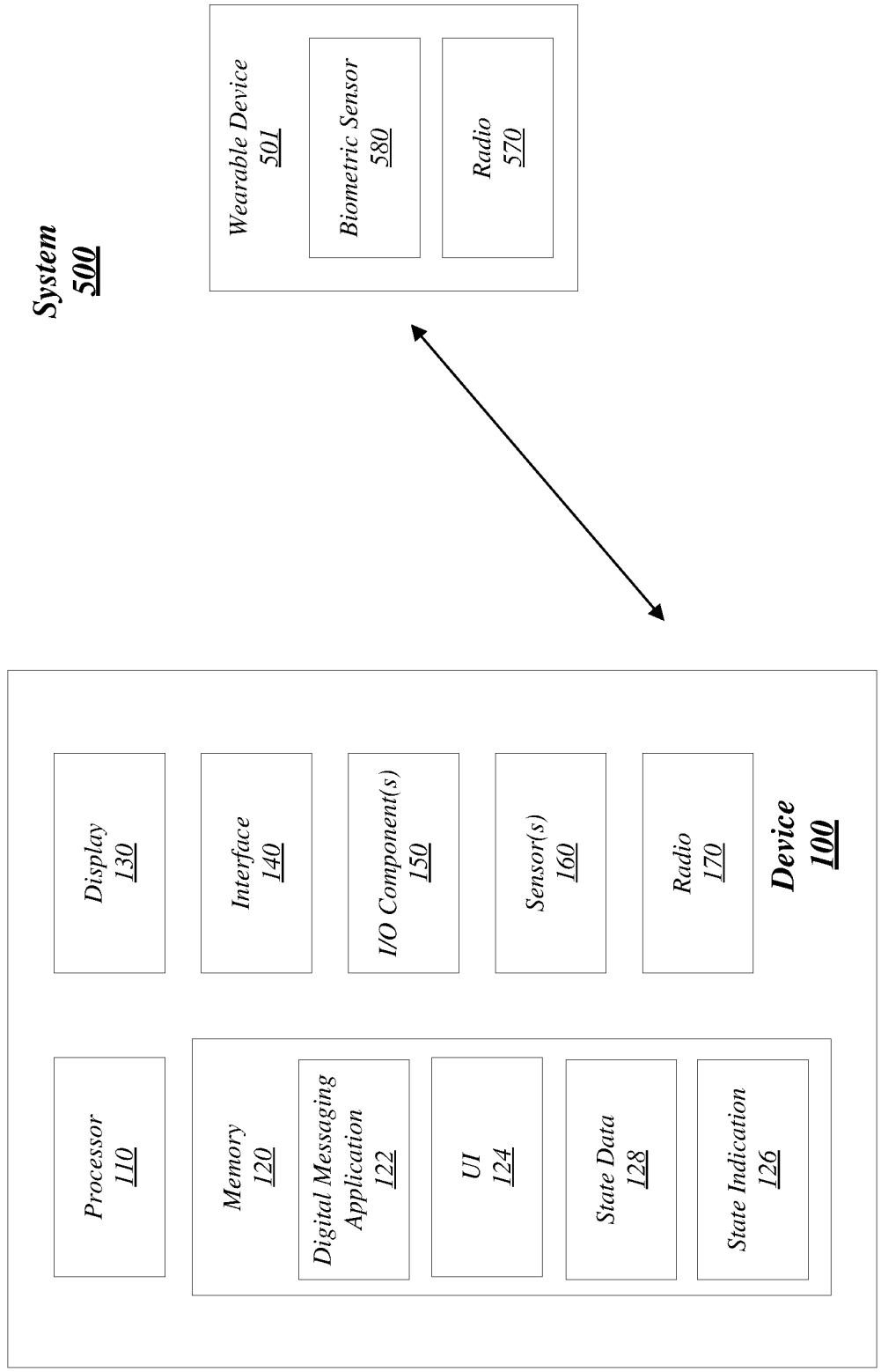
FIG. 5 illustrates a third example system.

FIG. 5 illustrates an example system 500 including computing device 100 of FIG. 1 coupled to a wearable device 501. The wearable device 501 can include, at least in part, a biometric sensor 480 and a radio 470.

With some examples, the biometric sensor 480 may include circuitry or processor logic arranged to capture any of a number of biometric indications. For example, biometric sensor 480 may be a heart rate sensor, a skin temperature sensor, an blood oxygen sensor, or the like.

Radio 470 can include circuitry arranged to communicate data with one or more other devices, such as computing device 100, via any of a variety of communication protocols. Such communication may involve communication across one or more networks, such a wireless local area networks (WLAN) or cellular network. In some examples, radio 470 can be arranged to communicate via Wi-Fi, Bluetooth, Zigbee, LTE, 5G, or the like.

During operation, wearable device 501 can capture indications of a biometric characteristics (e.g., heart rate) of a user or wearer of wearable device 501. Processor 110 of computing device 100, in executing digital messaging application 122, can receive indications of the biometric characteristic from wearable device 501. In particular, computing device 100 can receive indications of the biometric characteristic at a time or period coincident with presentation of message 180 via UI 124, or coincident with receipt of a response (or partial response) to message 180 or another message 180 from the user of computing device 100. State data 128 can include indications of the biometric characteristic received from wearable device 501.

Figure 6:
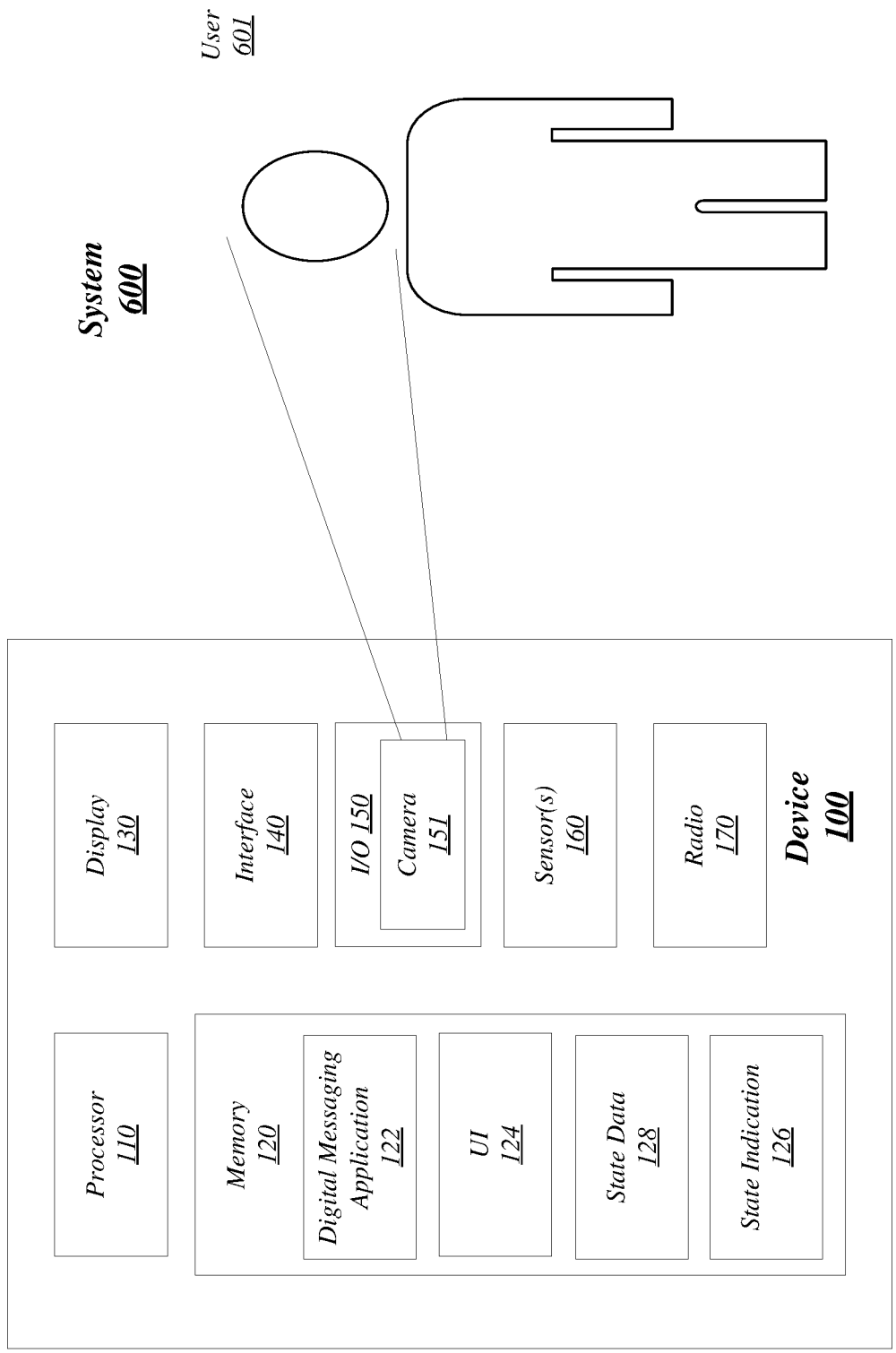
FIG. 6 illustrates a fourth example system.

FIG. 6 illustrates an example system 600 including computing device 100 of FIG. 1 and a user 601 of computing device 100. During operation, processor 110 of computing device 100, in executing digital messaging application 122, can cause an image of user 601 to be captured via a camera 151. In particular, computing device 100 can capture an image of user 601, via camera 151, at a time or period coincident with presentation of message 180 via UI 124, or coincident with receipt of a response (or partial response) to message 180 or another message 180 from the user of computing device 100. State data 128 can include indications of the image of the user captured via camera 151.

Figure 7:
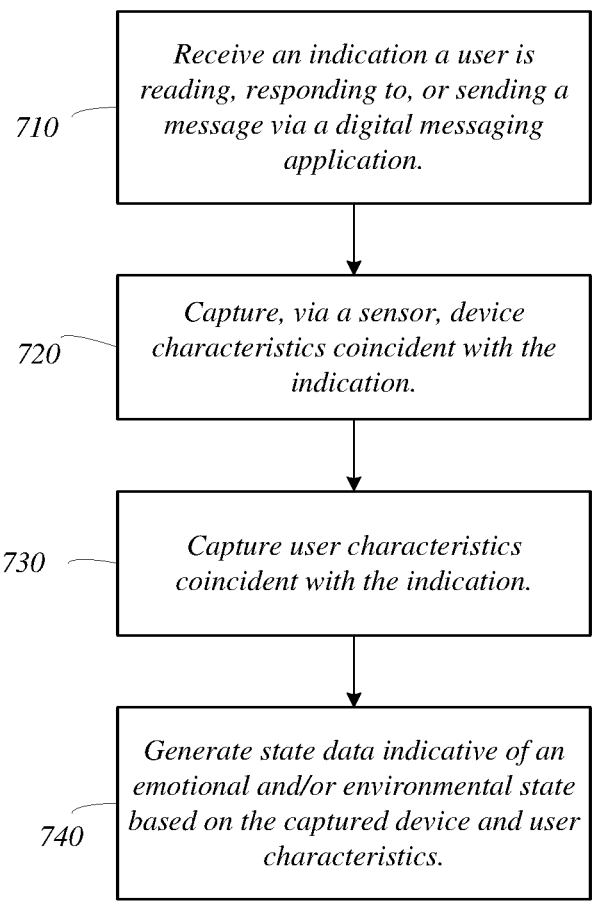
FIG. 7 illustrates an example logic flow.

FIG. 7 illustrates a logic flow 700 to generate state data. A computing device executing a digital messaging application can generate state data using logic flow 700. For example, computing device 100 of FIG. 1A can generate state data 128 using logic flow 700. In some implementations, a computing device (e.g., computing device 201) as part of technique 300 can use logic flow 700 to generate state data 128.

Logic flow 700 may begin at block 710. At block 710 "receive an indication a user is reading, responding to, or sending a message via a digital message application" computing device 100 can receive an indication that a user is reading and/or responding to a message. For example, processor 110 in executing digital messaging application 122 can receiving an indication that a user has read message 180-2 presented in message block 182-2. As another example, processor 110 in executing digital messaging application 122 can receive an indication that a user is responding to or sending a message. More specifically, processor 110 in executing digital messaging application 122 can receive input via input block 184.

Continuing to block 720 "capture, via a sensor, device characteristics coincident with the indication" computing device 100 can capture, via sensor(s) 180 device characteristics coincident with the indication from block 710. For example, processor 110 in executing digital messaging application can capture velocity and location information for computing device 100 via sensor(s) 180 (e.g., GPS sensor, or the like) at a time or period associated with when the indication at block 710 is received.

Continuing to block 730 "capture user characteristics coincident with the indication" computing device 100 can capture user characteristics coincident with the indication from block 710. For example, processor 110 in executing digital messaging application can capture biometric characteristics for a user of computing device 100 (e.g., via a connected wearable device 501, or the like) at a time or period associated with when the indication at block 710 is received. As another example, processor 110 in executing digital messaging application can capture an image of a user of computing device 100 (e.g., via camera 151, or the like) at a time or period associated with when the indication at block 710 is received. For another example, processor 110 in executing digital messaging application can capture characteristics of a user of computing device 100, such as, typing speed, typing pressure, or the like at a time or period associated with when the indication at block 710 is received.

It is important to note, that logic flow 700 can include either or both of blocks 720 and 730. For example, logic flow 700 could only include block 720 or block 730. Continuing to block 740 "generate state data indicative of an emotional and/or environmental state based on the captured device and user characteristics" computing device 100 can generate state data 128 indicative of an emotional and/or environmental state of the user of computing device 100 based on the captured device and user characteristics. For example, processor 110 in executing digital messaging application can generate state data 128 from device characteristics captured at block 720. As another example, processor 110 in executing digital messaging application can generate state data 128 from user characteristics captured at block 730. In still another example, processor 110 in executing digital messaging application can generate state data 128 from device characteristics captured at block 720 and from user characteristics captured at block 730.

FIGS. 7-12 illustrate example state indications. Such example state indications can be presented in a UI of a digital messaging application to provide an indication of an emotional and/or environmental state of a user. In some implementations, elements of system 200 of FIG. 2 can generate and present state indication 126 using technique 300.

Figure 8:
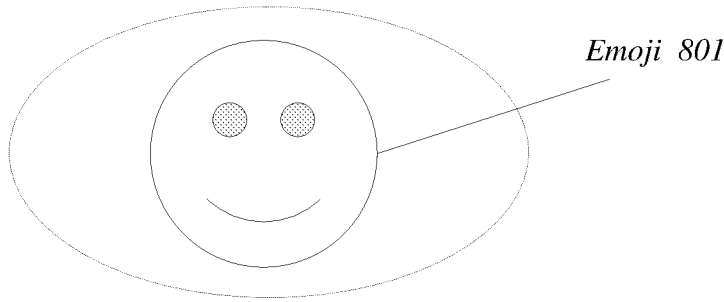
FIG. 8 illustrates a first example state indication.

Turning more particularly to FIG. 8, state indication 800 is depicted. State indication 800 can include an emoji 801. For example, the smiley face emoji is depicted as emoji 801. It is to be appreciated that a variety of emojis indicative of emotion and environment could be selected, for example, based on state data 128. As a specific example, the smiley face emoji could be selected as emoji 801 based on state data 128 indicative of a happy emotion. As another example, the car emoji could be selected as emoji 801 based on state data 128 indicative of the user being in a vehicle. As a further example, the angry face emoji could be selected as emoji 801 based on state data 128 indicative of the user being angry or agitated.

Figure 9:
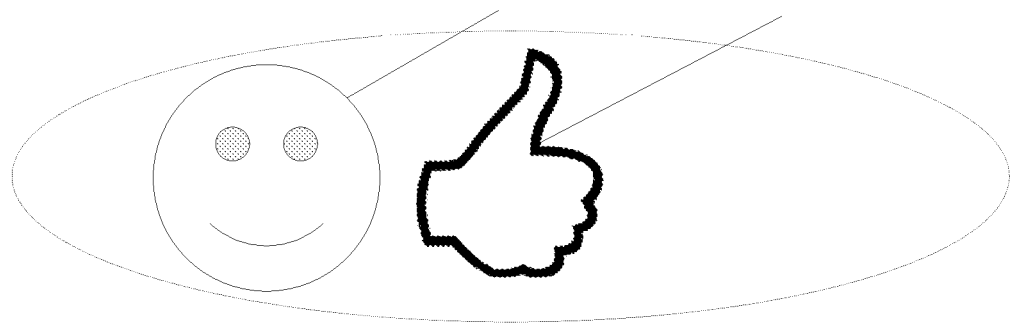
FIG. 9 illustrates a second example state indication.

Turning more particularly to FIG. 9, state indication 900 is depicted. State indication 900 can include multiple emojis 901. For example, state indication 900 includes emojis 901-1 and 901-2. Specifically, the state indication 900 includes smiley face emoji as emoji 901-1 and the thumbs up emoji as emoji 901-2. It is to be appreciated that a variety of emojis indicative of emotion and environment could be selected, for example, based on state data 128.

Figure 10:
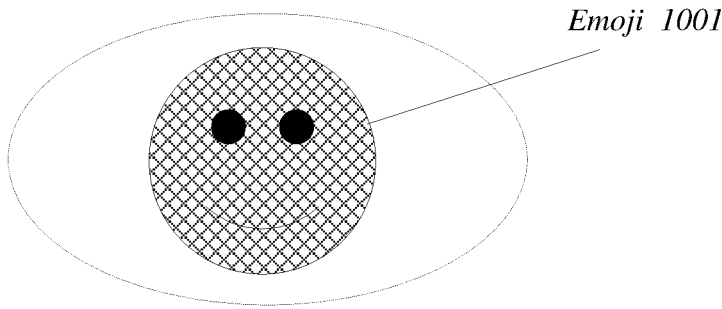
FIG. 10 illustrates a third example state indication.

Turning more particularly to FIG. 10, state indication 1000 is depicted. State indication 1000 can include a number of 1001 of a selected color or shading. For example, state indication 1000 includes emoji 1001 with dark shading. In some examples, a color or shading for the state indication can be selected based on state data 128. Coloring can be selected to further indicate an emotional or environmental state. As a specific example, the color red could be applied to indicators of the state indication 1000 to indicate an angry emotion.

Figure 11:
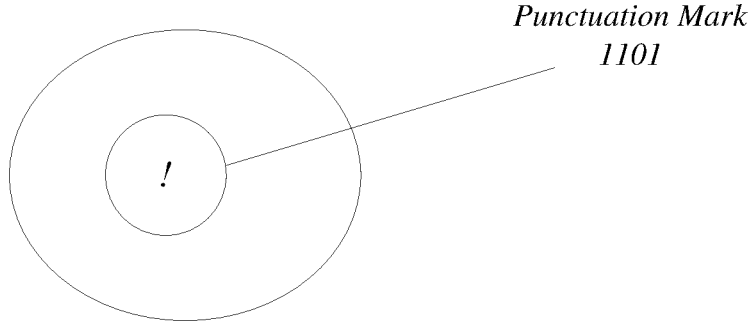
FIG. 11 illustrates a fourth example state indication.

Turning more particularly to FIG. 11, state indication 1100 is depicted. State indication 1100 can include a punctuation mark 1101. For example, the exclamation point punctuation mark is depicted as punctuation mark 1101. It is to be appreciated that a variety of punctuation marks indicative of emotion and/or environment could be selected, for example, based on state data 128. As a specific example, the punctuation exclamation point punctuation mark could be selected as punctuation mark 1101 based on state data 128 indicative of an excited emotion. As another example, the question mark punctuation mark could be selected as punctuation mark 1101 based on state data 128 indicative of the user being in a state of questioning of disbelief.

Figure 12:
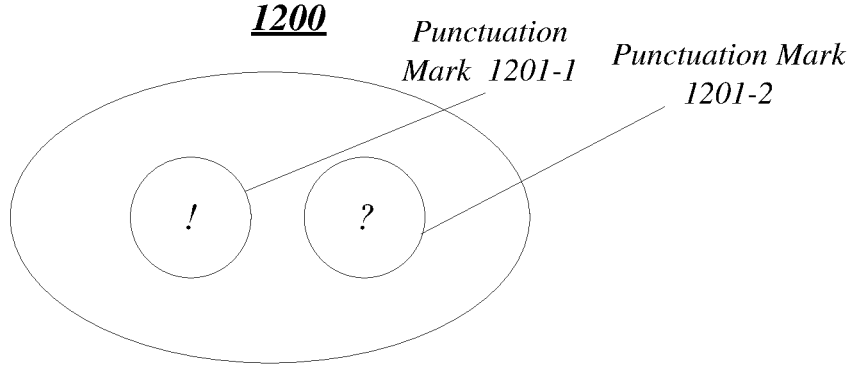
FIG. 12 illustrates a fifth example state indication.

Turning more particularly to FIG. 12, state indication 1200 is depicted. State indication 1200 can include multiple punctuation marks 1201. For example, state indication 1200 includes punctuation marks 1201-1 and 1201-2. Specifically, the state indication 1200 includes the exclamation point punctuation mark as punctuation mark 1201-1 and the question mark punctuation mark as punctuation mark 1201-2. It is to be appreciated that a variety of punctuation marks indicative of emotion and/or environment could be selected, for example, based on state data 128.

Figure 13:
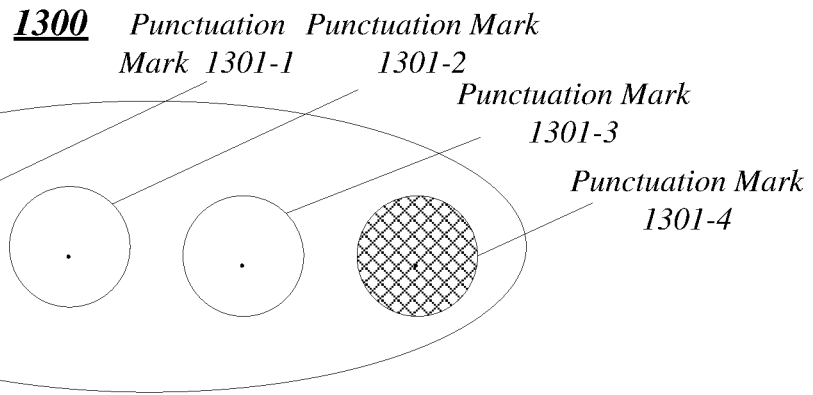
FIG. 13 illustrates a sixth example state indication.

Turning more particularly to FIG. 13, state indication 1300 is depicted. State indication 1300 can include one or more punctuation marks 1301. For example, state indication 1300 includes punctuation marks 1301-1, 1301-2, 1301-3, and 1301-4 all as periods. It is noted, that the punctuation marks 1301 could be any number or combination of punctuation marks, such as, for example, exclamation points, question marks, pound symbols, periods, etc. Furthermore, one of the punctuation marks 1301 is colored. For example, punctuation mark 1301-4 is depicted as colored or shaded. In some examples, a color or shading for the state indication can be selected based on state data 128. Coloring can be selected to further indicate an emotional or environmental state. As a specific example, the color red could be applied to indicators of the state indication 1300 to indicate an angry emotion.

Figure 14:
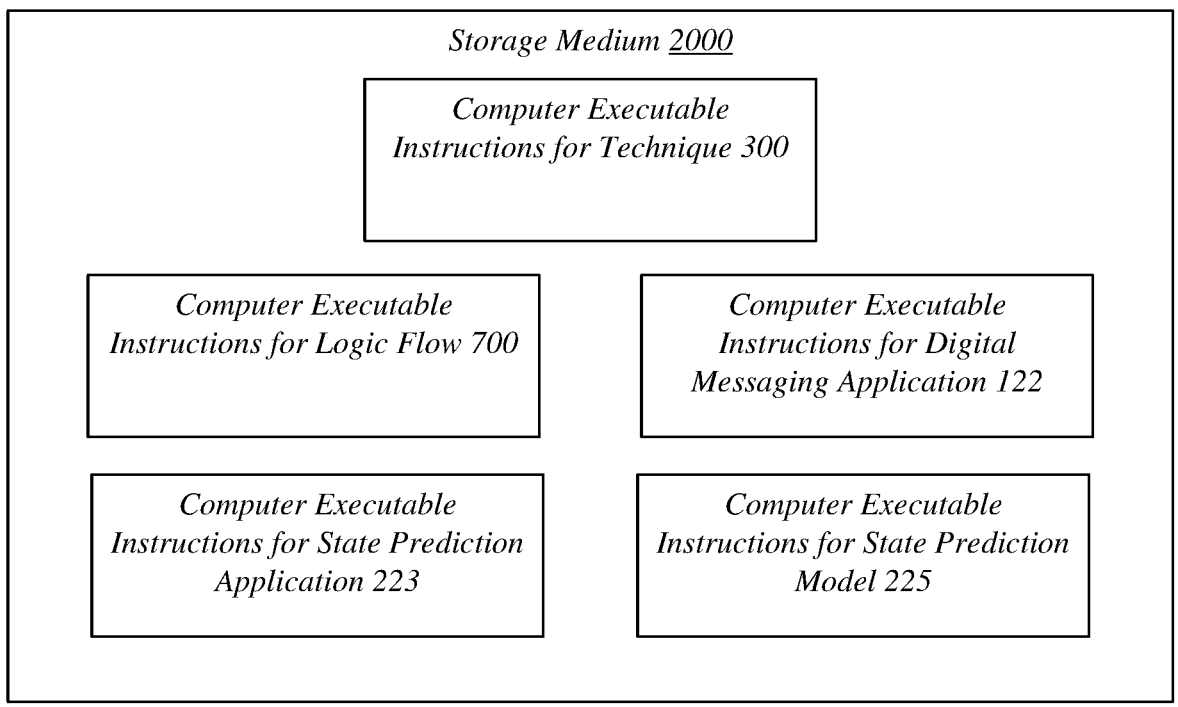
FIG. 14 illustrates an example storage medium.

FIG. 14 illustrates an embodiment of a storage medium 2000. Storage medium 2000 may comprise any non-transitory computer-readable storage medium or machine-readable storage medium, such as an optical, magnetic or semiconductor storage medium. In various embodiments, storage medium 2000 may comprise an article of manufacture. In some embodiments, storage medium 2000 may store computer-executable instructions, such as computer-executable instructions to implement one or more of logic flows or operations described herein, such as with respect to 300 and/or 700 of FIGS. 3 and/or 7. The storage medium 2000 may further store computer-executable instructions for the digital messaging application 122, the state prediction application 223, and the state prediction model 225. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited in this context.

Figure 15:
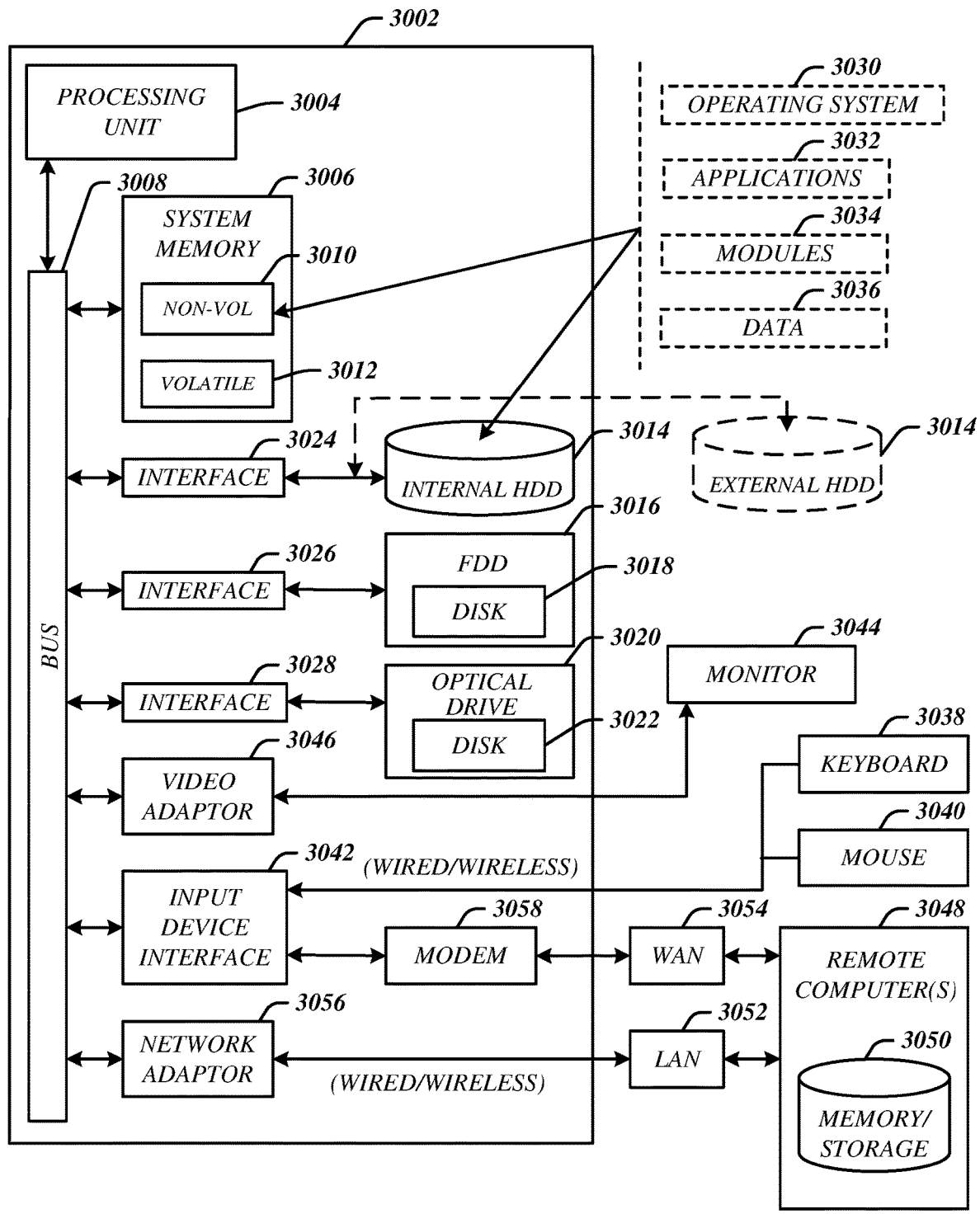
FIG. 15 illustrates an computer architecture.

FIG. 15 illustrates an embodiment of an exemplary computing architecture 3000 that may be suitable for implementing various embodiments as previously described. In various embodiments, the computing architecture 3000 may comprise or be implemented as part of an electronic device. In some embodiments, the computing architecture 3000 may be representative, for example, of a processor server that implements one or more components of the computing device 100, 201, 203 or the server 205. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 3000. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 3000 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 3000.

As shown in this figure, the computing architecture 3000 comprises a processing unit 3004, a system memory 3006 and a system bus 3008. The processing unit 3004 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 3004.

The system bus 3008 provides an interface for system components including, but not limited to, the system memory 3006 to the processing unit 3004. The system bus 3008 can be any of several types of bus structure that may further interconnect to a memory bus (with or without a memory controller), a peripheral bus, and a local bus using any of a variety of commercially available bus architectures. Interface adapters may connect to the system bus 3008 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 3006 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in this figure, the system memory 3006 can include non-volatile memory 3010 and/or volatile memory 3012. A basic input/output system (BIOS) can be stored in the non-volatile memory 3010.

The computer 3002 may include various types of computer-readable storage media in the form of one or more lower speed memory units, including an internal (or external) hard disk drive (HDD) 3014, a magnetic floppy disk drive (FDD) 3016 to read from or write to a removable magnetic disk 3018, and an optical disk drive 3020 to read from or write to a removable optical disk 3022 (e.g., a CD-ROM or DVD). The HDD 3014, FDD 3016 and optical disk drive 3020 can be connected to the system bus 3008 by a HDD interface 3024, an FDD interface 3026 and an optical drive interface 3028, respectively. The HDD interface 3024 for external drive implementations can include at least one or both of Universal Serial Bus (USB) and IEEE interface technologies.

The drives and associated computer-readable media provide volatile and/or nonvolatile storage of data, data structures, computer-executable instructions, and so forth. For example, a number of program modules can be stored in the drives and memory units 3010, 3012, including an operating system 3030, one or more application programs 3032, other program modules 3034, and program data 3036. In one embodiment, the one or more application programs 3032, other program modules 3034, and program data 3036 can include, for example, the various applications and/or components of the wire-free charging system 100.

A user can enter commands and information into the computer 3002 through one or more wire/wireless input devices, for example, a keyboard 3038 and a pointing device, such as a mouse 3040. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 3004 through an input device interface 3042 that is coupled to the system bus 3008 but can be connected by other interfaces such as a parallel port, IEEE 994 serial port, a game port, a USB port, an IR interface, and so forth.

A monitor 3044 or other type of display device is also connected to the system bus 3008 via an interface, such as a video adaptor 3046. The monitor 3044 may be internal or external to the computer 3002. In addition to the monitor 3044, a computer typically includes other peripheral output devices, such as speakers, printers, and so forth.

The computer 3002 may operate in a networked environment using logical connections via wire and/or wireless communications to one or more remote computers, such as a remote computer 3048. The remote computer 3048 can be a workstation, a server computer, a router, a personal computer, portable computer, microprocessor-based entertainment appliance, a peer device or other common network node, and typically includes many or all of the elements described relative to the computer 3002, although, for purposes of brevity, only a memory/storage device 3050 is illustrated. The logical connections depicted include wire/wireless connectivity to a local area network (LAN) 3052 and/or larger networks, for example, a wide area network (WAN) 3054. Such LAN and WAN networking environments are commonplace in offices and companies, and facilitate enterprise-wide computer networks, such as intranets, all of which may connect to a global communications network, for example, the Internet.

When used in a LAN networking environment, the computer 3002 is connected to the LAN 3052 through a wire and/or wireless communication network interface or adaptor 3056. The adaptor 3056 can facilitate wire and/or wireless communications to the LAN 3052, which may also include a wireless access point disposed thereon for communicating with the wireless functionality of the adaptor 3056.

When used in a WAN networking environment, the computer 3002 can include a modem 3058, or is connected to a communications server on the WAN 3054, or has other means for establishing communications over the WAN 3054, such as by way of the Internet. The modem 3058, which can be internal or external and a wire and/or wireless device, connects to the system bus 3008 via the input device interface 3042. In a networked environment, program modules depicted relative to the computer 3002, or portions thereof, can be stored in the remote memory/storage device 3050. It will be appreciated that the network connections shown are exemplary and other means of establishing a communications link between the computers can be used.

The computer 3002 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

What is claimed is:

1. An apparatus, comprising:
a processor; and
a memory coupled to the processor, the memory comprising instructions that when executed by the processor cause the processor to:
receive, from a messaging device, state data related to a message received at the message device, wherein the state data was determined based on characteristics of how a user interacted with the messaging device and characteristics of the messaging device in response to the message received at the messaging device;
generate a state indication based in part on the state data, using a state prediction model, the state indication including:
an indication of an emotional state of the user of the messaging device, and
an indication of an environmental state of the user of the messaging device;
generate an information element including the state indication; and
send the information element to a digital message application of the message device, the information element including the state indication to the messaging device, wherein a representation of the state indication may be presented for a transient period.

2. The apparatus of claim 1, wherein the received state data is related to:
a biometric data of a receiver of the received message;
a current usage of the messaging device;
an image of a receiver of the message; or
an environmental characteristic associated with the messaging device received from a sensor of the messaging device.

3. The apparatus of claim 2, wherein the indication of the emotional state is based at least in part on the received state data related to the biometric data.

4. The apparatus of claim 2, wherein the indication of the emotional state is based at least in part on the received state data related to the current usage of the apparatus.

5. The apparatus of claim 2, wherein the indication of the emotional state is based at least in part on the received state data related to the image in the state data.

6. The apparatus of claim 2, wherein the indication of the environmental state is based at least in part on the received state data related to the environmental characteristic.

7. The apparatus of claim 1, wherein the state data includes information related to an actively used application executed by the messaging device.

8. The apparatus of claim 1, wherein the state indication includes at least one emoji related to the indication of the emotional state.

9. The apparatus of claim 1, wherein the state indication includes a plurality of emojis, a first one of the plurality of emojis indicative of a first emotional or an environmental state and a second one of the plurality of emojis indicative of a second, different, indication of the emotional state or indication of the environmental state.

10. The apparatus of claim 1, wherein the state indication includes a plurality of punctuation marks.

11. The apparatus of claim 1, wherein the indication of the emotional state of a receiver of the received message, is based, in part, on the received state data indicating a state of connection of at least one accessory to the messaging device.

12. A non-transitory computer readable medium embodied with programming code executable by a processor that cause the processor to:
receive, from a messaging device, state data related to a message received at the messaging device, wherein the state data was determined based on characteristics of how a user interacted with the messaging device and characteristics of the messaging device;
generating a state indication based in part on the state data, using a state prediction model, the state indication including: an indication of an emotional state of the user of the messaging device, and
an indication of an environmental state of the user of the messaging device;
generate an information element including the state indication; and
send the information element to a digital message application of the message device, the information element including the state indication with a message requesting a transient presentation of an additional message related to the emotional state and the environmental state in a user interface of the messaging device.

13. The non-transitory computer readable medium of claim 12, wherein the received state data is related to:
a biometric data of a receiver of the received message;
a current usage of the messaging device;
an image of a receiver of the message;
an environmental characteristic associated with the messaging device received from a sensor of the messaging device; or
an actively used application executed by the messaging device.

14. The non-transitory computer readable medium of claim 13, wherein the:
indication of the emotional state is based at least in part on the biometric data,
the current usage of the processor,
the image in the state data, or
the environmental characteristic.

15. The non-transitory computer readable medium of claim 12, wherein the generated state indication includes:
at least one emoji related to the indication of the emotional state;
a plurality of emojis, a first one of the plurality of emojis indicative of a first emotional state or a first environmental state and a second one of the plurality of emojis indicative of a second, different from the first, emotional state or environmental state; or
a plurality of punctuation marks.

16. The non-transitory computer readable medium of claim 12, wherein the indication of the emotional state of a receiver of the received message is based, in part, on the received state data indicating an actively used application executed by the messaging device or a state of connection of at least one accessory to the messaging device.

17. A method comprising:
receiving, at a server from a messaging device, state data related to a received message, wherein the state data was determined based on characteristics of how a user interacted with the messaging device in response to the message received at the messaging device and characteristics of the messaging device;

at the server, generating a state indication based in part on the state data, using a state prediction model, the state indication including: an indication of emotional state of the user of the messaging device, and an indication of an environmental state of the user of the messaging device;

generating an information element including the state indication; and sending the information element to a digital message application of the message device, the information element including the state indication with a message requesting transient presentation of the emotional state and the environmental state as an additional message in a user interface of the messaging device.

18. The method of claim 17, wherein the received state data is related to:

a biometric state of a receiver of the received message;
a current usage of the messaging device;
an image of a receiver of the message;
an environmental characteristic associated with the messaging device received from a sensor of the messaging device; or an actively used application executed by the messaging device.

19. The method of claim 17, wherein the indication of:

the emotional state is based at least in part on the indication of the biometric state;
the emotional state is based at least in part on a current usage of the messaging device;
the emotional state is based at least in part on an image in the state data; or
the environmental state is based at least in part on the environmental characteristic.

20. The method of claim 17, wherein the generated state indication includes:

at least one emoji related to the indication of the emotional state;
a plurality of emojis, a first one of the plurality of emojis indicative of a first emotional or environmental state and a second one of the plurality of emojis indicative of a second, different, emotional or environmental state; or
a plurality of punctuation marks.

* * * * *